(12) United States Patent
Matsunami et al.

(10) Patent No.: US 7,629,134 B2
(45) Date of Patent: Dec. 8, 2009

(54) SOUR TASTE RECEPTOR COMPOSITIONS AND METHODS

(75) Inventors: Hiroaki Matsunami, Durham, NC (US); Momoka Matsunami, Durham, NC (US); Yoshiro Ishimaru, Tokyo (JP)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 11/825,941

(22) Filed: Jul. 10, 2007

(65) Prior Publication Data

US 2008/0081345 A1    Apr. 3, 2008

Related U.S. Application Data

(60) Provisional application No. 60/819,675, filed on Jul. 10, 2006.

(51) Int. Cl.
| G01N 33/53 | (2006.01) |
| G01N 33/567 | (2006.01) |
| C07K 1/00 | (2006.01) |
| C07K 14/00 | (2006.01) |
| C07K 17/00 | (2006.01) |

(52) U.S. Cl. ........................................ 435/7.2; 530/350
(58) Field of Classification Search ................... None
See application file for complete search history.

(56) References Cited

U.S. PATENT DOCUMENTS

| 6,608,176 | B2 | 8/2003 | Chaudhari |
| 6,955,887 | B2 | 10/2005 | Adler |
| 7,223,551 | B2 | 5/2007 | Adler |
| 7,297,543 | B2 | 11/2007 | Zoller |
| 7,309,577 | B2 | 12/2007 | Zoller |
| 7,344,859 | B2 | 3/2008 | Zoller |
| 7,364,867 | B2 | 4/2008 | Margolskee |
| 7,364,903 | B2 | 4/2008 | Zoller |
| 7,399,601 | B2 | 7/2008 | Adler |
| 2002/0164645 | A1 | 11/2002 | Zuker |
| 2004/0132075 | A1 | 7/2004 | Elliot |
| 2004/0132134 | A1 | 7/2004 | Adler |
| 2004/0171042 | A1 | 9/2004 | Adler |
| 2004/0209286 | A1 | 10/2004 | Adler |
| 2004/0248123 | A1 | 12/2004 | Drayna |
| 2005/0287517 | A1 | 12/2005 | Adler |
| 2006/0019346 | A1 | 1/2006 | Xu |
| 2007/0065884 | A1 * | 3/2007 | Zuker et al. ................. 435/7.2 |
| 2009/0089888 | A1 * | 4/2009 | Zuker et al. ..................... 800/3 |

OTHER PUBLICATIONS

Adler et al., 2000, "A Novel Family of Mammalian Taste Receptors," Cell 100:693-702.

Barr and Sternberg, "A polycystic kidney-disease gene homologue required for male mating behavior in *C. elegans*," 1999, Nature 401:386-389.

Barr et al., 2001, "The *Caenorhabditis elegans* autosomal dominant polycystic kidney disease gene homologs lov-1 and pkd-2 act in the same pathway," Curr. Biol. 11:1341-1346.

Behrens, et al., "Members of RTP and REEP Gene Families Influence Functional Bitter Taste Receptor Expression," The Journal of Biological Chemistry, vol. 281, No. 29, pp. 20650-20659, Jul. 21, 2006.

Chandrashekar et al., 2000, "T2Rs Function as Bitter Taste Receptors," Cell 100:703-711.

Chen et al., 1999, "Polycystin-L is a calcium-regulated cation channel permeable to calcium ions," Nature 401:386-386.

Clapham, 2003, "TRP channels as cellular sensors," Nature 426:517-524.

Clapp et al., 2001, "Immunocytochemical evidence for co-expression of Type III IP3 receptor with signaling components of bitter taste transduction," Neurosci. 2:6.

Corey et al., 2004, "TRPA1 is a candidate for the mechanosensitive transduction channel of vertebrate hair cells," Nature 432:723-730.

Damak et al., 2003, "Detection of Sweet and Umami Taste in the Absence of Taste Receptor T1r3," Science 301:850-853.

Delmas et al., 2004, "Polycystins, calcium signaling, and human diseases," Biochem. Biophys. Res. Commun. 322:1374-1383.

Faus, 2000, "Recent developments in the characterization and biotechnological production of sweet-tasting proteins," Appl. Microbiol. Biotechnol. 53:145-151.

Ganzevles and Kroeze, 1987, "Effects of Adaptation and Cross-Adaptation to Common Ions on Sourness Intensity," Physiol. Behav. 40:641-646.

Gonzalez-Perrett et al., 2001, "Polycystin-2, the protein mutated in autosomal dominant polycystic kidney disease (ADPKD), is a Ca2+-permeable nonselective cation channel," Proc. Natl. Acad. Sci. 98:1182-1187.

Guo et al., 2000, "Identification and Characterization of a Novel Polycystin Family Member . . . ", Genomics 241-251.

(Continued)

*Primary Examiner*—Robert Landsman
(74) *Attorney, Agent, or Firm*—Casimir Jones SC

(57) ABSTRACT

The present invention relates to sour taste receptors and compositions and methods thereof. In particular, the present invention provides assays and methods of screening for ligands specific for sour taste receptors. Additionally, the present invention provides methods for screening for accessory proteins and mutations, polymorphisms and other potential sour taste receptor protein mutations that are associated with disease states, and therapeutic agents, ligands, and modulators of such proteins. The present invention also provides compositions and methods for modulating sour taste receptors in vitro and in vivo.

12 Claims, 2 Drawing Sheets

OTHER PUBLICATIONS

Hanaoka et al., "Co-assembly of polycystin-1 and -2 produces unique cation-permeable currents," 2000, Nature 408:990-994.

Hughes et al., 1999, "Identification of a human homologue of the sea urchin receptor for egg jelly: a polycystic kidney disease-like protein," Hum. Mol. Genet. 8:543-549.

International Search Report and Written Opinion from PCT/US2007/15288, Apr. 9, 2008.

Ishimaru, et al., "Transient receptor potential family members PKD1L3 and PKD2L1 form a candidate sour taste receptor," PNAS, Aug. 15, 2006, vol. 103, No. 33, pp. 12569-12574.

Kitagawa et al., 2001, "Molecular Genetic Identification of a Candidate Receptor Gene for Sweet Taste," Biochem. Biophys. Res. Comm. 283:236-242.

Kohmura et al., 2002, "Structure-taste relationships of the sweet protein monellin," Pure Appl. Chem. 74:1235-1242.

Jones, "Golf: An Olfactory Neuron Specific-G Protein Involved in Odorant Siognal Transduction," Science, May 19, 1989, vol. 244, pp. 790-795.

Li et al., 2002, "Human receptors for sweet and umami taste," Proc. Natl. Acad. Sci. 99:4692-4693.

Li et al., 2003, "Identification of two novel polycystic kidney disease-1-like genes in human and mouse genomes," Genomics 81:596-608.

Lindemann et al., 1996, "Taste Reception," Physiol. Rev. 76:718-66.

Lingueglia et al., 1997, "A Modulatory Subunit of Acid Sensing Ion Channels in Brain and Dorsal Root Ganglion Cells," J. Biol. Chem. 272:29778-29783.

Lopezjimenez, N.D., et al., "Two members of the TRPP family of ion channels, Pkd1l3 and Pkd2l1, are co-expressed in a subset of taste receptor cells," J. Neurochemistry. Jul. 2006, vol. 98, pp. 68-77.

Ludwig et al., 1998, "A family of hyperpolarization-activated mammalian cation channels," Nature 393:587-691.

Makhlouf and Blum, 1972, "Kinetics of the Taste Response to Chemical Stimulation: A Theory of Acid Taste in Man," Gastroenterology 63:67-75.

Margolskee, 2002, "Molecular Mechanisms of Bitter and Sweet Taste Transduction," J. Biol. Chem. 277:1-4.

Matsunami et al., 2000, "A family of candidate taste receptors in human and mouse," Nature 404:601-604.

Max et al., 2001, "Tas1r3, encoding a new candidate taste receptor, is allelic to the sweet responsiveness locus Sac," Nat Genet. 28:58-63.

Miyamoto et al., 2000, "Acid and salt responses in mouse taste cells," Prog. Neurobiol. 62:135-157.

Miyoshi et al., 2001, "IP3 receptor type 3 and PLCβ2 are co-expressed with taste receptors T1R and T2R in rat taste bud cells," Chem Senses 26:259-265.

Montell, 2005 Sci. STKE (Feb. 22, 2005), "The TRP Superfamily of Cation Channels,".

Montmayeur and Matsunami, 2002, "Receptors for bitter and sweet taste," Curr Opin. Neurobiol. 12:366-371.

Montmayeur et al., 2001, "A candidate taste receptor gene near a sweet taste locus," Nat. Neurosci 4:492-498.

Moosmang et al., 1999, "Differential Distribution of Four Hyperpolarization-Activated Cation Channels in Mouse Brain," Biol. Chem. 380:975-980.

Mueller et al., 2005, "The receptors and coding logic for bitter taste," Nature 434:225-229.

Nauli and Zhou, 2004, "Polycystins and mechanosensation in renal and nodal cilia," Bioessays 26:844-856.

Nauli et al., 2003, "Polycystins 1 and 2 mediate mechanosensation in the primary cilium of kidney cells," Nat Genet. 33:129-137.

Nelson et al., 2001, "Mammalian Sweet Taste Receptors," Cell 106:381-390.

Nelson et al., 2002, "An amino-acid taste receptor," Nature 416:199-202.

Nomura et al., 1998, "Identification of PKDL, a Novel Polycystic Kidney Disease 2-Like Gene Whose Murine Homologue is Deleted in Mice with Kidney and Retinal Defects," J. Biol. Chem. 273:25967-25973.

Perez et al., 2002, "A transient receptor potential channel expressed in taste receptor cells," Nat. Neurosci. 5:1169-1176.

Richter, T.A., et al., "Sour taste stimuli evoke Ca2+ and pH responses in mouse taste cells," J. Physiol (2003) 547:2, pp. 475-483.

Richter et al., 2004, "Acid-Sensing Ion Channel-2 is Not Necessary for Sour Taste in Mice," J. Neurosci. 24:4088-4091.

Scott, 2004, "The Sweet and the Bitter of Mammalian Taste," Curr. Opin Neurobiol. 14:423-427.

Stevens et al., 2001, "Hyperpolarization-activated channels HCN1 and HCN4 mediate responses to sour stimuli," Nature 413:631-635.

Ugawa et al., "Receptor that leaves a sour taste in the mouth," 1998, Nature 395:555-556.

Ugawa et al., 2003, "Amiloride-Insensitive Currents of the Acid-Sensing Ion Channel-2a(ASIC2a)/ASIC2b Heteromeric Sour-Taste Receptor Channel," J. Neurosci. 23:3616-3622.

Wong et al., 2002, "A p75NTR and Nogo receptor complex mediates repulsive signaling by myelin-associated glycoprotein," Nat. Neurosci. 5:1302-1308.

Yuasa et al., 2002, "The Sequence, Expression, and Chromosomal Localization of a Novel Polycystic Kidney Disease 1-Like Gene, PKD1L1, in Human," Genomics 79:376-386.

Zhang et al., 2003, "Coding of Sweet, Bitter, and Umami Tastes: Different Receptor Cells Sharing Similar Signaling Pathways," Cell 112:293-301.

Zhao et al., 2003, "The Receptors for Mammalian Sweet and Umami Taste," Cell 115:255-266.

Caicedo, A., et al., "Individual Mouse Taste Cells Respond to Multiple Chemical Stimuli," Journal of Physiology (2002), 544, pp. 501-509.

Drayna, D., (2005) "Human Taste Genetics", Annu Rev Genomics Hum Genet; 6:217-35.

Hoon, J., et al., "Putative Mammalian Taste Receptors: A Class of Taste-Specific GPCRs with Distinct Topographic Selectivity", Cell 96, 541-551 (1999).

Kim, U.K., et al., "Genetics of Human Taste Perception," (2004), J. Dent. Res. 83(6), 448-453.

Murakami, M., et al., Genomic Organization and Functional Analysis of Murine PKD2L1. (2005) J. Biol. Chem. 280, 5626-5635.

Saito, Harumi, et al., "RTP Family Members Induce Functional Expression of Mammalian Odorant Receptors," (2004), Cell, 119, 679-691.

Sugita, Makoto and Yoshiki Shiba, "Genetic Tracing Shows Segregation of Taste Neuronal Circuitries for Bitter and Sweet," Science, vol. 309, Jul. 29, 2005, pp. 781-785.

* cited by examiner

SOUR TASTE RECEPTOR COMPOSITIONS AND METHODS

This patent application claims priority to U.S. Provisional Patent Application No. 60/819,675 filed Jul. 10, 2006, herein incorporated by reference in its entirety.

This invention was made with government support under Grant No. 5 ROI DC005782 awarded by the National Institutes of Health. The government has certain rights in the invention.

FIELD OF THE INVENTION

The present invention relates to sour taste receptors and compositions and methods thereof. In particular, the present invention provides assays and methods of screening for ligands specific for sour taste receptors. Additionally, the present invention provides methods for screening for accessory proteins and mutations, polymorphisms and other potential sour taste receptor protein mutations that are associated with disease states, and therapeutic agents, ligands, and modulators of such proteins. The present invention also provides compositions and methods for modulating sour taste receptors in vitro and in vivo.

BACKGROUND OF THE INVENTION

Flavor is a complex mixture of sensory input composed of taste (gustation), smell (olfaction) and the tactile sensation of food as it is being munched, a characteristic that food scientists often term "mouthfeel." Although people may use the word "taste" to mean "flavor," in the strict sense it is applicable only to the sensations arising from specialized taste cells in the mouth. Scientists generally describe human taste perception in terms of four qualities: saltiness, sourness, sweetness and bitterness. A fifth taste exists as umami, the sensation elicited by glutamate, one of the 20 amino acids that make up the proteins in meat, fish and legumes. Glutamate also serves as a flavor enhancer in the form of the additive monosodium glutamate (MSG).

Animals use taste systems to evaluate the nutritious value, toxicity, sodium content, and acidity of the food they ingest. In vertebrates, taste reception occurs at the top of the taste cells that form taste buds, and each taste bud has an onion-like shape. There are four major taste areas where taste buds are concentrated; on the tongue at the circumvallate papilla, foliate papilla, and fungiform papilla, and the palate (top of the mouth). Circumvallate papillae, found at the very back of the tongue, contain hundreds to thousands of taste buds. By contrast, foliate papillae, localized to the posterior lateral edge of the tongue, contain dozens to hundreds of taste buds. Further, fungiform papillae, located at the front of the tongue, contain only a single or a few taste buds. Each taste bud, depending on the species, contains 50-150 cells, including precursor cells, support cells, and taste receptor cells (Lindemann et al., 1996, Physiol. Rev. 76:718-66). Receptor cells are innervated at their base by afferent nerve endings that transmit information to the taste centers of the cortex through synapses in the brain stem and thalamus. Elucidating the mechanisms of taste cell signaling and information processing is important to understanding the function, regulation, and perception of the sense of taste.

Much progress has been made in unraveling molecular mechanisms of bitter, sweet and umami taste in recent years (Margolskee, 2002, J. Biol. Chem. 277:1-4; Montmayeur and Matsunami, 2002, Curr. Opin. Neurobiol. 12:366-371; Scott, 2004, Curr. Opin. Neurobiol. 14:423-427). However, the molecular basis of sour taste sensation is the most poorly understood of the five basic modalities.

A whole industry exists around trying to disguise or mask unpleasant tastes. In 1879, Ira Remsen noticed that a derivative of coal tar tasted sweet. His finding led to the development of saccharin, an artificial sweetener today known as Sweet-n-Low Brand® sweetener. Today, many more artificial sweeteners with varying chemical structures are available including Sunett® (acesulfame potassium), NutraSweet® or Equal® (aspartame), Splenda® (sucralose), and Sugaree® (D-Tagatose). However, some of these artificial sweeteners, such as saccharin and aspartame, have been linked with cancer and other medical problems. Natural plant compounds have also been found to mask unpleasant tastes. Miraculin, a protein found in the pulp of the fruit of the miracle berry, an evergreen shrub native to West Africa, has been described as a "sweet-inducing" protein, and is suggested to bind to sweet taste receptors in the mouth when sour substances are present, the result being a strong sweet taste. Miraculin itself has no distinct taste, but the human tongue when exposed to the protein perceives ordinarily sour foods as sweet. Other plant proteins which are being studied as natural sweeteners include, stevia, curculin, mabinlin, monellin, pentadin, brazzein, and thaumatin (Faus, 2000, Appl. Microbiol. Biotechnol. 53:145-151; Kohmura et al., 2002, Pure Appl. Chem. 74:1235-1242). Contrasted to those individuals who prefer sweet tasting products, there are an equal number who seek out the taste of sour, as evidenced by the myriad of sour candy options available for consumption.

Sweeteners, either artificial or natural, find useful application, for example, as sugar substitutes in the weight loss industry, as sugar alternatives for people suffering from diabetes and other diseases where sugar intake is restricted, as additives to foods and beverages, and in the pharmaceutical industry to make medicaments palatable. Clinically, taste disorders are prevalent in patients undergoing chemotherapy and often have a negative impact on the quality of life and nutrition for those patients. Radiation treatment can also damage taste receptors, giving food a metallic taste. Those patients suffering from taste distortion may avoid foods with high nutritional value, such as fresh fruits and vegetables, thereby further depressing their immune functions. A better understanding of the complex and often multifactorial etiology of taste dysfunction would enable the clinician to institute measures to minimize the impact of these disturbing changes. What is needed is a better understanding of sour taste receptor sensation. What is further needed is a better understanding of sour taste receptor function. Additionally, what is needed are methods and assays to screen for, and to use, ligands that can either inhibit or upregulate sour taste receptor.

SUMMARY OF THE INVENTION

The present invention relates to sour taste receptors and compositions and methods thereof. In particular, the present invention provides assays and methods of screening for ligands specific for sour taste receptors. Additionally, the present invention provides methods for screening for accessory proteins and mutations, polymorphisms and other potential sour taste receptor protein mutations that are associated with disease states, and therapeutic agents, ligands, and modulators of such proteins. The present invention also provides compositions and methods for modulating sour taste receptors in vitro and in vivo.

The transient receptor potential (TRP) ion channel subunit genes were first defined in the *Drosophila* visual system, where TRP deficient flies were blinded by intense light as a result of calcium dependent adaptation disruption (Clapham et al., 2002, IUPHAR Compendium, TRP Channels). Since then, TRP ion channels have been implicated in various sensory systems, including vision, smell, pheromone, hearing, touch, osmolarity, thermosensation, and sweet, bitter and umami taste, in diverse animal species ranging from mammals and fish to fruit flies and nematodes (Clapham, 2003, Nature 426:517-524; Montell, 2005, Sci. STKE 2005:re3). Some TRP channels such as vanilloid receptor, TRPV1, function as receptors for stimuli (high temperature and capsaicin) by themselves, whereas other TRP channels, such as TRPM5, are downstream effectors of G protein coupled sensory receptors.

Two TRP channel family members, PKD1L3 and PKD2L1, are co-expressed in a subset of taste receptor cells in specific taste areas. Cells expressing these molecules are different from bitter, sweet or umami sensing cells. The PKD2L1 proteins are accumulated at the taste pore region, where taste chemicals are detected. Finally, PKD1L3 and PKD2L1 are activated by sour chemicals when co-expressed in heterologous cells. Therefore, PKD1L3 and PKD2L1 heteromers function as sour taste receptors.

In one embodiment, the present invention relates to a method for identifying a sour taste receptor ligand, comprising providing a sample comprising a sour taste receptor, and a test compound, exposing said test compound to said sample and measuring the activity of said sour taste receptor in said sample in response to said test compound. In some embodiments, said sample is a cell line expressing PKD1L3 and PKD2L1. In some embodiments, said cell line is a 293T cell line. In some embodiments, said cell line is derived from a 293T cell line, such as a Hana3A cell line or a 44 cell line. In some embodiments, said PKD1L3 and PKD2L1 are either human or murine. In some embodiments, said test compound is from a list consisting of a naturally occurring molecule, a synthetically derived molecule, or a recombinantly derived molecule.

In one embodiment, the method for identifying a sour taste receptor ligand further comprising a reporting agent. In some embodiments, the method for identifying a sour taste receptor ligand further comprises the step of detecting the presence or absence of a sour taste receptor ligand based upon said reporting agent activity. In some embodiments, said reporting agent is a fluorophore, and said fluorophore is from a group consisting of fluo-4 and fura-red.

In one embodiment, the present invention is a cell that expresses a heterologous sour taste receptor. In some embodiments, said cell line expresses murine or human PKD1L3 and PKD2L1, or combinations thereof. In some embodiments, said cell is a human embryonic kidney 293T cell line.

In some embodiments, the sour taste receptor is modulated, in vivo or in vitro, by the introduction of a modulator (e.g., ligand, chemical, compound, or agent) to a sample or subject such that the sour taste sensation is inhibited or decreased. In other embodiments, the modulator acts to upregulate or increase sour taste sensation. In some embodiments, the modulator is added or applied to a food product (e.g., vegetable, fruit, meat, candy, oils, etc.). In other embodiments, an inhibitor of the sour taste sensation is added or applied as part of a pharmaceutical medicament (e.g., pillules, powders, elixirs, etc.).

DEFINITIONS

Figure 1:
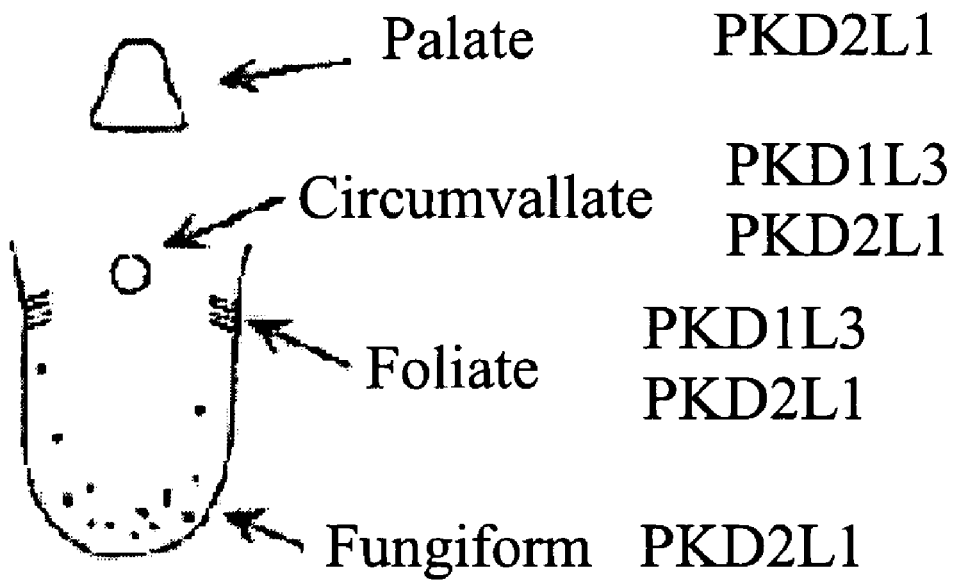
FIG. 1 shows the localization of PKD1L3 and PKD2L1 on the mouse tongue.

The term "test compound" refers to any chemical entity, pharmaceutical, drug, and the like that can be used to treat or prevent a condition, disease, illness, sickness, or disorder of bodily function, or otherwise alter the physiological or cellular status of a sample. Test compounds comprise both known and potential therapeutic compounds. A test compound can be determined to be by screening using the screening methods of the present invention.

The term "sample" as used herein is used in its broadest sense. A sample suspected of containing a protein may comprise a cell, a portion of a tissue, an extract containing one or more proteins and the like.

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat Nos. 6,074,859; 5,976,796; 5,674,713; and 5,618,682; all of which are incorporated herein by reference), green fluorescent protein (e.g., GenBank Accession Number U43284), chloramphenicol acetyltransferase, β-galactosidase, alkaline phosphatase, horse radish peroxidase, and fluorophores such as fluo-4 and fura-red.

The term "siRNAs" refers to short interfering RNAs. Methods for the use of siRNAs are described in U.S. Patent App. No. 20030148519/A1 (herein incorporated by reference in its entirety). In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

As used herein, the term "genetic variation information" or "genetic variant information" refers to the presence or absence of one or more variant nucleic acid sequences (e.g., polymorphism or mutations) in a given allele of a particular gene (e.g., a PKD1L3 or PKD2L1 gene of the present invention).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "recombinant protein" or "recombinant polypeptide" as used herein refers to a protein molecule that is expressed from a recombinant DNA molecule.

The term "native protein" as used herein, is used to indicate a protein that does not contain amino acid residues encoded by vector sequences; that is the native protein contains only those amino acids found in the protein as it occurs in nature. A native protein may be produced by recombinant means or may be isolated from a naturally occurring source.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

DETAILED DESCRIPTION OF THE INVENTION

Bitter, sweet and umami stimuli are detected by G protein coupled receptors. Bitter chemicals are detected by around 30 T2R receptor family members (Adler et al., 2000, Cell 100: 693-702; Chandrashekar et al., 2000, Cell 100:703-711; Matsunami et al., 2000, Nature 404:601-604). Sweet and umami compounds are detected by different combinations of T1R family members. Sugars and sweeteners are detected by T1R2+T1R3 heteromers, whereas umami tasting 1-amino acids are detected by T1R1+T1R3 heteromers (Damak et al., 2003, Science 301:850-853; Kitagawa et al., 2001, Biochem. Biophys. Res. Comm. 283:236-242; Li et al., 2002, Proc. Natl. Acad. Sci. 99:4692-4693; Max et al., 2001, Nat. Genet. 28:58-63; Montmayeur et al., 2001, Nat. Neurosci 4:492-498; Nelson et al., 2002, Nature 416:199-202; Nelson et al., 2001, Cell 106:381-390; Zhao et al., 2003, Cell 115:255-266). Different sets of taste cells express T2Rs, T1R2+T1R3, or T1R1+T1R3. Moreover, an animal's preference toward chemicals can be manipulated by misexpressing foreign receptors in different subsets of taste cells. For example, when the artificial RASSL receptor was expressed in T1R2 positive sweet sensing cells, mice were attracted to water containing spiradonine, an agonist for the RASSL receptor, whereas when the same receptor was expressed in T2R expressing bitter sensing cells, the animals avoid spiradoline (Mueller et al., 2005, Nature 434:225-229; Zhao et al., 2003). Thus, taste cells are likely to be "labeled" as bitter, sweet, or umami sensing cells. Nevertheless, both T1Rs and T2Rs express common signal transduction molecules, including PLCb2 and TRPM5, and IP3R-3 (Clapp et al., 2001, Neurosci. 2:6; Miyoshi et al., 2001, Chem. Senses 26:259-265; Perez et al., 2002, Nat. Neurosci. 5:1169-1176; Zhang et al., 2003, Cell 112:293-301).

In contrast to sweet, bitter and umami sensations, molecular mechanisms of sensing sour and salty taste are poorly understood and even confusing, although a number of candidate receptors and transduction mechanisms have been proposed (Miyamoto et al., 2000, Prog. Neurobiol. 62:135-157). For example, acid-sensing ion channel-2 (ASIC2) is proposed to function as a sour receptor in the rat (Ugawa et al, 2003, J. Neurosci. 23:3616-3622; Ugawa et al., 1998, Nature 395:555-556). However, it is not expressed in mouse taste cells and not required for acid sensation (Richter et al., 2004, J. Neurosci. 24:4088-4091). HCN1 and HCN4, members of hyperpolarization-activated cyclic nucleotide gated channels (HCNs) are also candidate sour receptor channels (Stevens et al., 2001, Nature 413:631-635). However, calcium imaging experiments using taste bud slices did not support this possibility, as $Cs^+$, an inhibitor of HCN channels, did not block $Ca^{2+}$ response of taste cells to sour stimuli (Richter et al., 2003, J. Physiol. 547:475-483). Moreover, unlike bitter, sweet and umami taste receptors, SICS2, HCN1 and JCN4 are all widely expressed in the nervous system (Lingueglia et al., 1997, J. Biol. Chem. 272:29778-29783; Ludwig et al., 1998, Nature 393:587-591; Moosmang et al., 1999, Biol. Chem. 380:975-980).

Among TRP channel families, member of the PKD family (polycystic kidney disease, also called TRPP or polycystins) have unique properties (Delmas et al., 2004, Biochem. Biophys. Res. Commun. 322:1374-1383; Nauli and Zhou, 2004, Bioessays 26:844-856). Their founding members, PKD1 and PKD2, were identified as autosomal dominant polycystic kidney disease genes. PKD1 is a large protein with a long N-terminal extracellular domain followed by 11 transmembrane domains. PKD1 may not form functional ion channels, while PKD2 which has 6 transmembrane domains similar to other TRP members, can function as a non-selective cation channel. Importantly, PKD1 and PKD2 heteromer formation using their intracellular C-terminal regions is required to become a functional receptor/channel (Hanaoka et al., 2000, Nature 408:990-994). The heteromer of PKD1 and PKD2 are thought to sense mechanical flow, osmolarity and unknown extracellular ligand(s). In *C. elegans*, a PKD1 homolog, Lov-1, and a PKD2 homolog are expressed in male specific sensory neurons, localized at the chemosensory cilia, and are required for male mating behavior thereby suggesting their function as sensory receptors (Barr et al., 2001, Curr. Biol. 11:1341-1346; Barr and Sternberg, 1999, Nature 401:386-389). There are four additional PKD1-like and two additional PKD2-like genes found in the mouse or human genome (Chen et al., 1999, Nature 401:383-386; Guo et al., 2000, Genomics 241-251; Hughes et al., 1999, Hum. Mol. Genet. 8:543-549; Li et al., 2003, Genomics 81:596-608; Nomura et al., 1998, J. Biol. Chem. 273:25967-25973; Yuasa et al., 2002, Genomics 79:376-386), however the biological functions of these PKD related molecules are poorly understood.

Figure 2:
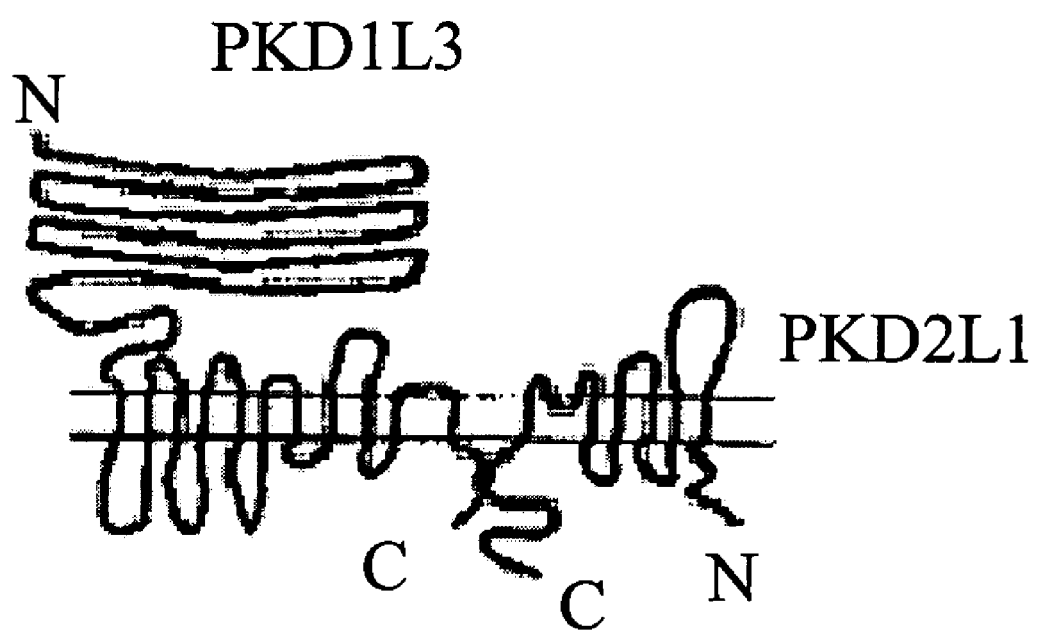
FIG. 2 shows a potential mechanism for cell surface formation of the PKD1L3 and PKD2L1 heteromer.

Characterization of molecular identities that receive taste chemicals is needed to understand the molecular mechanisms underlying taste sensation. Two TRP channel members, PKD1L3 (Genbank Accession Nos. AY164486 (murine, nucleic acid, SEQ ID NO:1), AAO32799 (murine, amino acid, SEQ ID NO:2), AY164485 (human, nucleic acid, SEQ ID NO:3) and AAO32798 (human, amino acid, SEQ ID NO:4), incorporated herein by reference in their entireties) and PKD2L1 (Genbank Accession Nos. NM_181422 (murine, nucleic acid, SEQ ID NO:5), NP_852087 (murine, amino acid, SEQ ID NO:6), NM_016112 (human, nucleic acid, SEQ ID NO:7) and NP_057196 (human, amino acid, SEQ ID NO:8), incorporated herein by reference in their entireties) are specifically expressed in a subset of taste receptor cells that do not correspond to bitter, sweet or umami sensing cells (FIG. 1). The proteins are localized at the apical tip of taste cells where tastants are detected. PKD1L3 and PKD2L1 heteromer formation (FIG. 2) is required for functional cell surface expression and whenever they are expressed in heterologous cells they are activated by sour solutions. Therefore, PKD1L3 and PKD2L1 function together as sour taste receptors in mammals, although an understanding of the mechanism is not necessary to practice the present invention and the present invention is not limited to any particular mechanism of action.

In one embodiment, the present invention provides methods for detecting ligands, and other modulators, that interact with the sour taste receptor. In some embodiments, the methods are assays that comprise the PKD1L3 and PKD2L1 proteins, or functional fragments or variants thereof. In some embodiments, the assays comprise human PKD1L3 and PKD2L1 proteins, or functional fragments thereof. In some embodiments, these two proteins are co-expressed in tissue culture cells lines, or other cell samples (e.g., gross tissue, tissue explants, primary cells, etc.). In some embodiments, these two proteins are chimeric proteins, whereas one or more of the protein domains is murine in origin while one or more of the protein domains are of human origin. In some embodiments, test compounds suspected, or known to be, ligand to sour taste receptors are applied to the sample and sour taste sensation in the sample is subsequently monitored following application of the test compound. In some embodiments, the monitoring of the sour taste sensation in a sample is performed by monitoring calcium influx via fluorescence, although the present invention is not limited by the manner in which activity or binding is monitored. In some embodiments, the ligand inhibits the sour taste sensation, whereas in other embodiments the ligand enhances the sour taste sensation.

In some embodiments, the PKD1L3 and/or PKD2L1 amino acid sequences are altered or are provided as part of a chimeric peptide sequence, such as with an affinity tag to assist with purification, with a localization tag to assist with intracellular trafficking or localization, and the like). For example, in some embodiments the sequences of the proteins are linked, directly or indirectly, (e.g., via a linker) with an affinity tag (e.g., hemagglutinin A (HA) tag, Rho tag, and the like), for example on the N-terminus of the protein.

In some embodiments, the present invention provides variants or fragments thereof of the wild-type PKD1L3 and/or PKD2L1 gene or gene product sequences. For example, a wild-type gene or gene product has the characteristics of that gene or gene product when isolated from a naturally occurring source. A wild-type gene is that which is most frequently observed in a population and is thus arbitrarily designed the "normal" or "wild-type" form of the gene. In contrast, modified, mutant and variant refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product. This is in contrast to synthetic mutants that are changes made in a sequence through human (or machine) intervention.

Variants may be generated by post-translational processing of the protein (e.g., by enzymes present in a producer strain or by means of enzymes or reagents introduced at any stage of a manufacturing process) or by mutation of the structural gene. Mutations may include site deletion, insertion, domain removal and replacement mutations.

Structural and functional equivalents and variants are contemplated with the present invention. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of sensory receptors, such as sour taste receptors PKD1L3 and PKD2L1 disclosed herein that contain conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., Biochemistry, pg. 17-21, $2^{nd}$ ed, WH Freeman and Co., 1981). Whether a change in the amino acid sequence of a peptide results in a functional homolog can be readily determined by assessing the ability of the variant peptide to function in a fashion similar to the reference protein. Peptides having more than one replacement can readily be tested in the same manner.

As well, a variant of the present invention includes "non-conservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

In some embodiments, the methods and compositions of the present invention are combined with compositions and methods of other taste receptors (e.g., sweet, salty, bitter, umami). Examples of taste receptor compositions and methods which can be combined or utilized with the compositions and methods of the present invention include, but are not limited to, those found in the following United States Patent and Patent Applications, all of which are incorporated herein by reference in their entireties; U.S. Pat. Nos. 6,955,887, 6,608,176, 20060019346, 20050287517, 20050084932, 20040248123, 20040348149, 20040229239, 20041219632, 20040209313, 10040209286, 20040191862, 20040175793, 20040175792, 20040171042, 20040132134, 20040132075, 20020164645, 20020151052, 20020037515. These applications also describe screening methods and compound libraries that find use with the present invention.

In one embodiment, the present invention provides methods of identifying modulators of the sour taste receptor. A modulator can be a candidate or test substance that is suspected of modulating (e.g., increasing, decreasing, inhibiting) the activity of the sour taste receptor. As used herein, the terms "candidate substance" and "test substance" are used interchangeably, and each refers to a substance that is suspected to interact with either PKD1L3, PKD2L1 or the heteromer, including any synthetic, recombinant, or natural product or composition. A test substance suspected to interact with either PKD1L3 or PKD2L1 or the heteromer can be evaluated for such an interaction using the methods disclosed herein. In some embodiments, test substances include, but are not limited to peptides, oligomers, nucleic acids (e.g., aptamers), small molecules (e.g., chemical compounds), antibodies or fragments thereof, nucleic acid-protein fusions, any other affinity agent, and combinations thereof. A test substance can additionally comprise a carbohydrate, a vitamin or derivative thereof, a hormone, a neurotransmitter, a virus or receptor binding domain thereof, a pheromone, a toxin, a growth factor, a platelet activation factor, a neuroactive peptide, or a neurohormone.

In some embodiments, a candidate substance elicits no sour taste sensation. In some embodiments, a candidate substance elicits an increased, or enhanced, sour taste sensation. In some embodiments, a candidate substance to be tested can be a purified molecule, a homogenous sample, or a mixture of molecules or compounds. In some embodiments, the test substance is a small molecule. Small molecules may be comprised in compound libraries of diverse or structurally similar compounds (e.g., combinatorial chemistry synthesized libraries). In some embodiments, the test substance will include naturally occurring sour compounds (e.g., derived from plant extracts and the like). Test substances can be obtained or prepared as a library. As used herein, the term "library" means a collection of molecules. A library can contain a few or a large number of different molecules, varying from about ten molecules to several billion molecules or more. A molecule can comprise a naturally occurring molecule, a recombinant molecule, or a synthetic molecule. A plurality of test substances in a library can be assayed simultaneously. Optionally, test substances derived from different libraries can be pooled for simultaneous evaluation. Representative libraries include but are not limited to a peptide library (U.S. Pat. Nos. 6,156,511, 6,107,059, 5,922,545, and 5,223,409), an oligomer library (U.S. Pat. Nos. 5,650,489 and 5,858,670), an aptamer library (U.S. Pat. Nos. 6,180,348 and 5,756,291), a small molecule library (U.S. Pat. Nos. 6,168, 912 and 5,738,996), a library of antibodies or antibody fragments (U.S. Pat. Nos. 6,174,708, 6,057,098, 5,922,254, 5,840,479, 5,780,225, 5,702,892, and 5,667,988), a library of nucleic acid-protein fusions (U.S. Pat. No. 6,214,553), and a library of any other affinity agent that can potentially bind to a T2R76 polypeptide (e.g., U.S. Pat. Nos. 5,948,635, 5,747, 334, and 5,498,538). Additionally, a library can comprise a random collection of molecules. Alternatively, a library can comprise a collection of molecules having a bias for a particular sequence, structure, or conformation (e.g., U.S. Pat. Nos. 5,264,563 and 5,824,483, incorporated herein in their entireties). Methods for preparing libraries containing diverse populations of various types of molecules are known in the art, for example as described in U.S. patents cited herein above. Numerous libraries are also commercially available.

In some embodiments, ligands that inhibit sour taste sensation are used in the pharmaceutical industry to create more palatable medicaments. In some embodiments, ligands that inhibit sour taste sensation are suitable for oral administration and may be presented as adjuvants in capsules, cachets or tablets, wherein the medicament preferably contains a predetermined amount of ligand sufficient to inhibit the sour taste sensation.

In some embodiments, ligands that inhibit sour taste sensation are used with food products and beverages. In some embodiments, ligands that inhibit sour taste sensation are added to, applied to, or applied on, food products that impart a sour taste sensation (e.g., for example, broccoli and green grapes). In some embodiments, ligands that inhibit sour taste sensation are added to beverages (e.g., for example, grapefruit juice, lime juice and lemon juice).

In one embodiment, the present invention relates to compositions and methods relating to RNA inhibition of the sour taste receptor. In some embodiments, the translation of either PKD1L3 or PKD2L1 is inhibited by application of a short interfering siRNA (siRNA). In some embodiments, the siRNA targets the expression of one or both of the murine sour taste receptor proteins. In some embodiments, the siRNA targets the expression of one or both of the human sour taste receptor proteins.

In one embodiment, the present invention relates to compositions and methods for inhibition of the sour taste receptor by using an antibody to either PKD1L3 or PKD2L1, or both, or fragments thereof. In some embodiments, antibodies are administered with pharmaceutical medicaments and treatments. In some embodiments, the antibodies are co-administered with food stuffs (e.g., broccoli, cauliflower, spinach, etc.) that trigger sour taste receptors.

In one embodiment, the present invention relates to compositions and methods for inhibition of the sour taste receptor by using a small molecule to PKD1L3, PKD2L1, or both, or fragments thereof. In some embodiments, the small molecules are administered with pharmaceutical medicaments and treatments. In some embodiments, the small molecules are co-administered with food stuffs (e.g., broccoli, cauliflower, spinach, etc.) that trigger sour taste receptors.

In one embodiment, the methods of the present invention are used to define ligands that enhance sour taste sensation. In some embodiments, ligands that enhance sour taste sensation are added to human consumable products, such as candy, gummy worms, powdered candy, chewing gum, libations and elixirs.

In one embodiment, PKD1L3 and PKD2L1 can be used to created transgenic animals (e.g., mice, rats, hamsters, guinea pigs, ungulates, zebrafish, pigs, birds, etc.). In some embodiments, the transgenic animals are created such that the sour taste receptor is overexpressed. In some embodiments, the transgenic animals are created such that sour taste receptor expression is knocked out (e.g., does not express the receptor). In some embodiments, the transgenic animal has one of PKD1L3 or PKD2L1 genes knocked out. In other embodiments, the transgenic animal has both PKD1L3 and PKD2L1 genes knocked out. In some embodiments, the transgenic animal expresses one or both of human PKD1L3 and PKD2L1. In some embodiments, the transgenic animals express a chimeric protein for PKD1L3, PKD2L1 or both. Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. No. 5,573,933 (transgenic pigs); U.S. Pat. No. 5,162,215 (transgenic avian species) and U.S. Pat. No. 5,741,957 (transgenic bovine species), all patents being incorporated herein by reference in their entireties.

In one embodiment, computer modeling and searching technologies are used to identify compounds, or improvements of already identified compounds, that can modulate the sour taste receptor expression or activity. Having identified such a compound or composition, the active sites or regions are identified. Such active sites might typically be ligand binding sites, such as the interaction domains of a portion of a ligand with the sour taste receptor itself (e.g., either PKD1L3 or PKD2L1 alone, or the heteromer), or the interaction domains of a ligand with the wild-type sour taste receptor in comparison to the interaction domains of ligand with a mutant (e.g., change in the nucleic acid or amino acid sequence, or deletions, insertions, truncations of a gene or protein) sour taste receptor. In some embodiments, the active site can be identified using methods known in the art including, for example, from the amino acid sequences of peptides, from the nucleotide sequences of nucleic acids, or from study of complexes of the relevant compound or composition with its natural ligand. In some embodiments, chemical or X-ray crystallographic methods can be used to find the active site by finding where on the heteromer the complexed ligand is found. In some embodiments, the three dimensional geometric structure of the active site is determined (e.g., by known methods including X-ray crystallography). In further embodiments, solid or liquid phase nuclear magnetic resonance can be used to determine certain intra-molecular distances. In some embodiments, partial or complete geometric structures of the heteromer alone, or with ligand interaction, is accomplished by high resolution electron microscopy. For example, the geometric structures can be measured with a complexed ligand, natural or artificial, thereby increasing the accuracy of the active site structure. In another embodiment, the structure of the wild-type sour taste receptor is compared to that of a mutant sour taste receptor. In some embodiments, rather than solve the entire structure, the structure is solved for the protein domains that are changed between the wild type and mutant sour taste receptor.

In one embodiment, the present invention provides cells expressing wild type or chimeric PKD1L3 and/or PKD2L1 proteins. In some embodiments, the cells are human cells. In some embodiments, the human cells are human embryonic kidney 293T cells. In some embodiments, the cells are murine in origin. In some embodiments, the wild type proteins are murine in origin, whereas in other embodiments the wild type proteins are human in origin. In some embodiments, the chimeric protein contains domains, regions, or fragments of both human and murine PKD1L3 and/or PKD2L1 proteins. In some embodiments, the chimeric proteins express domains, regions, or fragments of human and/or murine PKD1L3 and/or PKD2L1 in conjunction with non-human or non-murine homologous protein domains (e.g., *Xenopus*, zebrafish, *C. elegans*, for example). In some embodiments, the cells comprise a chimeric PKD1L3 and/or PKD2L1 proteins are used to study structure/function relationships, and other assays to characterize sour taste receptor activity and function.

In some embodiments, derivatives of human embryonic kidney 293T cells are used for optimal expression of human PKD1L3 and/or PKD2L1 proteins or fragments thereof at the cell membrane. In some embodiments, a derived human embryonic kidney 293T cell line is a Hana3A cell line configured to express, via stable or transient transfection, one or more of receptor transporting proteins (e.g., RTP1, RTP2), receptor expressing enhancer proteins (e.g., REEP1) (Behrens et al., 2006, J. Biol. Chem. 281:20650-20659; incorporated herein by reference in its entirety), and/or the olfactory neuron specific G-protein $G_{olf}$-protein (Jones & Reed, 1989, Science 244:790-795, incorporated herein by reference in its entirety). In some embodiments, a further derivation of the Hana3A cell line is the "44" cell line configured to express, via stable or transient transfection, one or more of brain synembrin (Ric8B), the heat shock protein 70 (HSP70) homolog HSC70T, and/or an RTP1A1 protein. For example, expression of human PKD1L3 and human PKD2L1 in the cell membrane of 44 cells expressing one or more of Ric8B, HSC70T and/or RTP1A1 is enhanced as compared to expression is Hana3A cells or 293T cells.

EXAMPLES

Example 1

In Situ Hybridizations

Procedures for non-radioactive hybridization were previously described (Saito et al., 2004, Cell 119:679-691). Briefly, digitonin (Dig) labeled RNA probes were hybridized, washed and detected by alkaline phosphatase conjugated anti-Dig antibodies followed by incubation with NBT/BCIP. For two-color fluorescent in situ hybridization, RNA probes were labeled with Dig or FITC (Roche). FITC labeled probes were detected by horse radish peroxidase (HRP) conjugated anti-FITC antibodies followed by TSA-Cy3 (Perkin-Elmer). HRP was inactivated by incubating with PBS containing 1% hydrogen peroxide for 30 min., and Dig labeled probes were detected by HRP conjugated anti-Dig followed by TSA-FITC.

Example 2

Immunoprecipitation

Protocols used for immunoprecipitation were previously described in Saito et al, 2004.

Example 3

Cell Surface Protein Expression

Protocols used for cell surface expression of proteins were previously described in Saito et al., 2004.

Example 4

Cell Culture, Gene Cloning and Calcium Imaging

Cell tissue culture was performed as previously described in Saito et al., 2004. The PKD1L3 gene (SEQ ID NO:1) was cloned into the mammalian expression vector pDisplay (Invitrogen), and the PKD2L1 gene (SEQ ID NO:5) was cloned into the mammalian expression vector pCI (Promega). For calcium imaging, pDisplay-PKD1L3 and/or pCI-PKD2L1 were transfected into cells (previously seeded on glass coverslips) using Lipofectamine 2000 (Invitrogen). Following incubation, the transfected cells were loaded with fluo-4 (Molecular Probes) and fura-red (Molecular Probes) for 45 min. at room temperature prior to analysis.

RESULTS

The mouse genome contains at least 33 TRP channel members. To identify TRP ion channel members functioning in taste transduction, in suit hybidizations were performed using probes against all 33 TRP channel members (Corey et al., 2004, Nature 432:723-730) against sections of circumvallate papilla of the mouse taste tissue. Probes for TRPM5 labeled a subset of taste cells, and probes for PKD1L3 and PKD2L1 also hybridized to taste cells. A similar expression pattern was observed with rat circumvallate papilla. Other TRP channels did not show robust expression in taste cells.

In circumvallate papilla, around 20% of the taste cells expressed PKD1L3 and PKD2L1. To examine the expression of PKD1L3 and PKD2L1 in different taste areas, in situ hybridization with sections from circumvallate, foliate and fungiform papilla, and palate was performed. PKD2L1 expression was observed in a subset of taste cells in all four different taste areas, whereas PKD1L3 expression was only seen in circumvallate and foliate papillae. Additional in situ hybridization experiments did not reveal significant expression of other PKD family members in fungiform papilla or palate.

To investigate the correlation of TRPM5, PKD1L3 and PKD2L1 expression cells in taste buds, double-labeled fluorescent in situ hybridizations were performed. In circumvallate and foliate papilla, almost all of the PKD1L3 positive cells were also PKD2L1 positive, indicating these two molecules are expressed in the same cells. In contrast, TRPM5 signals did not co-localize with PKD2L1 or PKD1L3 indicating different taste cells express TRPM5 and PKD1L3/PKD2L1. In fungiform papilla and palate, PKD2L1 positive cells were PKD1L3 negative, confirming the absence of PKD1L3 expression in these two areas.

To examine mRNA expression of PKD1L3 and PKD2L1 in different tissues, RT-PCR was performed using mRNA for 16 different tissues including taste tissues (circumvallate and foliate papillae). Both PKD1L3 and PKD2L1 were abundantly expressed only in taste tissues and testis, whereas they were absent or only faintly expressed in all other tissues tested (GAPDH positive control RT-PCR showed expression in all tissues).

Taste reception occurs at the taste pore where the apical tip of each taste cell dendrite topped with microvilli is accumulated. To demonstrate the co-localization of PKD1L3 and PKD2L1 at the apical tip of the taste cell dendrite, antibodies against PKD2L1 were generated to analyze the PKD2L1 cellular localization within the taste cells. Immunostaining with rat and mouse circumvallate and foliate taste tissues demonstrate that PKD2L1 localized at the apical end of a subset of taste cells at the taste pore area, with weaker labeling throughout the positive cells. Preincubation of the antibody with peptide antigen (10 ng/ml) abolished the taste cell staining, thereby confirming the specificity of the antibody. Monoclonal IP3R-3 antibody marks PLCb2 and TRPM5 expressing bitter, sweet and umami sensing cells (Clapp et al., 2001; Miyoshi et al., 2001). Double staining using antibodies against PKD2L1 and IP3R-3 revealed different sets of taste cells were expressing PKD2L1 and IP3R-3, consistent with mRNA expression analysis. Therefore, the interaction between PKD1L3 and PKD2L1 is consistent with the role for PKD1L3 and PKD2L1 in taste reception.

Since Hanaoka et al. (2000) had previously suggested that the C-terminal cytoplasmic domains of related PKD1 and PKD2 domains interacted and created functional channel expression, experiments were performed to investigate whether PKD1L3 and PKD2L1 also formed functional heteromeric receptors. Cell surface expression of PKD1L3 was investigated with and without the presence of PKD2L1. PKD1L3 was tagged with HA at the N-terminal extracellular domain. When PKD1L3 was expressed alone in HEK293T cells, no cell surface expression was observed when compared to control BFP signals (PKD1L3 was observed when the cells were permeabilized and stained demonstrating cytoplamic expression). It had been previously demonstrated by Murakami et al. (2005, J. Biol. Chem. 280:5626-5635) that PKD2L1 alone is not transported to the cell surface in heterologous cells. Therefore, interaction between the two molecules is necessary for their cell surface expression.

Bitter taste receptors (T2Rs) and sweet and umami receptors (T1Rs) are co-expressed with TRPM5, PLCb2 and IP3R-3 proteins. Since PKD1L3 and PKD2L1 positive cells do not co-localize with TRPM5 or IP3R-3 positive cells, it was tested whether these two proteins were involved in another taste sensation; such as sour or salty. To examine whether PKD1L3/PKD2L1 function as taste receptors, calcium imaging experiments were carried out using HEK293T cells transiently expressing PKD1L3 and/or PKD2L1. The cells were transfected with expression vectors encoding PKD1L3 and/or PKD2L1, loaded with calcium sensitive dyes (fluo-4 and fura-red), and stimulated with various taste chemicals and osmolarity solutions. When calcium concentration inside the cell is upregulated upon stimulation with ligands, the fluo-4 signal increases whereas the fura-red signal decreases, thereby allowing ratiometric measurements of intracellular calcium concentration (Wong et al., 2002, Nat. Neurosci. 5:1302-1308). It was demonstrated that cells expressing both PKD1L3 and PKD2L1 responded to solutions containing citric acid (25 mM, pH 2.6), whereas cells expressing either PKD1L3 or PKD2L1, or neither of them, showed little or no calcium response when treated with citric acid. When extracellular calcium ions were eliminated from the bath solution, the calcium response from citric acid was abolished, demonstrating that calcium ion were coming from the extracellular solution. The experiments demonstrate that PKD1L3 and PKD2L1 form functional channels that are activated by citric acid. Citric acid elicits a more sour response at the same pH when compared to hydrochloric acid. Consistent to this notion, hydrochloric acid at the same pH caused much less of a calcium response in cells expressing both proteins. Further, function of the two protein heteromer was not inhibited by the ASIC inhibitor amiloride or the HCN inhibitor Cs+. Additionally, PKD1L3/PKD2L1 did not respond to salt (NaCl), bitter chemicals (quinine, cyclohexamide, PROP), sucrose, saccharin, or the umami compounds l-glutamate and IMP. Therefore, heteromers of PKD1L3 and PKD2L1 function as sour taste receptors.

PKD1L3 has homology to PKD1; both have a large extracellular domain followed by eleven transmembrane domains, whereas PKD2L1 is similar to PKD2; both have six transmembrane domains like most of the TRP channel members. PKD1 does not appear to function as an ion-conducting channel, but rather plays a role in sensing mechanical flow, whereas PKD2 forms a functional ion-conducting channel (Gonzalez-Perrett et al., 2001, Proc. Natl. Acad. Sci. 98:1182-1187; Nauli et al., 2003, Nat. Genet. 33:129-137). Chen et al. (1999) showed that PKD2L1 was capable of forming a functional calcium permeable channel, whereas it was not known whether PKD1L3 alone could form an ion-conducting channel. Calcium imaging experiments found that acid stimulation (e.g., citric, hydrochloric, maleic) opens calcium permeable channels. The present invention is not limited to a particular mechanism. Indeed, an understanding of the mechanism is not necessary to practice the present invention. Nonetheless, it is contemplated that PKD1L3 functions as a sour sensing receptor and PKD2L1 functions as an ion-conducting channel. An additional possibility is contemplated, in that PKD2L1 functions as a sour receptor and PKD3L1 functions as a facilitator of PKD2L1 expression.

Sour sensation is not a simple measurement of pH in a solution. For example, at the same pH, citric acid or acetic acid tastes more sour than hydrochloric acid (Ganzevles and Kroeze, 1987, Physiol. Behav. 40:641-646; Makhlouf and Bum, 1972, Gastroenterology 63:67-75). Similarly, calcium imaging experiments using mouse taste tissue slices showed that citric acid is a more potent sour ligand than hydrochloric acid at the same pH (Richter et al., 2003). The present invention is not limited to a particular mechanism. Indeed, an understanding of the mechanism is not necessary to practice the present invention. Nonetheless, it is contemplated that sour taste receptors do not function as mere acid pH sensors. The experiments presented herein demonstrate that citric acid is more potent than hydrochloric acid in activating PKD1L3/PKD2L1 heteromers at the same pH. It is contemplated that citrate ions or an undissolved form of citric acid interacts with PKD1L3 and/or PKD2L1 and enhances the sensitivity of the hydrogen activated receptor. A similar mechanism can be found in umami taste sensations, where some nucleotides such as IMP potentiate the activation of the umami receptor T1R1/T1R3 to 1-amino acids (Li et al., 2002; Nelson et al., 2002).

It is not well understood why both PKD1L3 and PKD2L1 are needed for cell surface expression. The present invention is not limited to a particular mechanism. Indeed, an understanding of the mechanism is not necessary to practice the present invention. Nonetheless, it is contemplated that as the C-terminal cytoplasmic domain of PKD2L1 contains endoplasmic reticulum (ER) retention signals (Murakami et al., 2005), the C-terminal cytoplasmic domain of PKD1L3 also contains ER retention signals and the interactions between PKD2L1 and PKD1L3 mask these signals, thereby allowing the complex to be transported to the cell surface.

Previous studies have shown that different taste cells are responsible for sensing bitter, sweet or umami taste. It is demonstrated herein that PKD1L3/PKD2L1 expressing cells are segregated from TRPM5 and IP3R-3 expressing bitter, sweet or umami taste cells, thereby demonstrating that a subset of cells are sour sensing cells. Additionally, Caicedo et al. (2002, J. Physiol. 544:501-509; Richter et al., 2003) have shown that 23-25% of taste cells are activated by citric acid with calcium imaging of taste bud slices. This correlated with the present findings that approximately 20% of taste cells express PKD1L3 and PKD2L1.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for identifying a compound that modulates the activity of a sour taste receptor, comprising:
   a) providing
      i) a first sample comprising recombinant cells which have been genetically engineered to express a functional sour taste receptor comprised of PKD1L3 protein and PKD2L1 protein, and
      ii) a second sample comprising cells which do not express said functional sour taste receptor comprised of PKD1L3 protein and PKD2L1 protein;
   b) contacting said first sample with at least one compound;
   c) contacting said second sample with said at least one compound;
   d) measuring calcium levels in said first sample and said second sample in the presence and absence of said at least one compound; and
   e) identifying said compound as a sour taste receptor modulator if it elicits a detectable change in calcium levels in said first sample in comparison to said second sample.

2. The method of claim 1, wherein said either or both of said first and second samples is a 293T cell line.

3. The method of claim 1, wherein said PKD1L3 and PKD2L1 are either human or murine.

4. The method of claim 1, wherein said test compound is selected from the group consisting of a naturally occurring molecule, a synthetically derived molecule, and a recombinantly derived molecule.

5. The method of claim 1, wherein said first and second samples comprise a calcium sensitive dye.

6. The method of claim 5, wherein said calcium sensitive dye is a fluorophore.

7. The method of claim 6, wherein said fluorophore is from a group consisting of fluo-4 and fura-red.

8. The method of claim 1, wherein said method is conducted under in vitro conditions.

9. The method of claim 1, wherein said method is conducted under ex vivo conditions.

10. The method of claim 1, wherein said method is conducted under in vivo conditions.

11. The method of claim 1, wherein said cells within said second sample are selected from the group consisting of cells expressing bitter taste receptors, cells expressing sweet taste receptors, and cells expressing umami taste receptors.

12. The method of claim 1, wherein said second sample is a 293T cell line.

* * * * *